(12) United States Patent
Hugo

(10) Patent No.: US 6,206,697 B1
(45) Date of Patent: Mar. 27, 2001

(54) DEVICE FOR THE RETENTION AND ADAPTATION OF A MATRIX FOR DENTAL RESTORATIONS

(75) Inventor: Burkhard Hugo, Hettstadt (DE)

(73) Assignee: Geno Know-How Sarnen AG, Sarnen (CH)

( * ) Notice: Subject to any disclaimer, the term of this patent is extended or adjusted under 35 U.S.C. 154(b) by 0 days.

(21) Appl. No.: 09/436,723

(22) Filed: Nov. 9, 1999

(51) Int. Cl.$^7$ .................................................. A61C 5/04
(52) U.S. Cl. ........................... 433/155; 433/39; 433/139
(58) Field of Search .................... 433/155, 39, 139, 433/149

(56) References Cited

U.S. PATENT DOCUMENTS

| | | | |
|---|---|---|---|
| 348,628 | * 9/1886 | Hewett | 433/39 |
| 388,620 | * 8/1888 | Booth | 433/39 |
| 427,338 | * 5/1890 | Marshall | 433/149 |
| 3,628,249 | 12/1971 | Wurl | 433/149 |
| 4,004,345 | 1/1977 | Ely | 433/40 |
| 4,715,816 | * 12/1987 | Mogelof | 433/139 |
| 5,527,181 | * 6/1996 | Rawls et al. | 433/149 |
| 5,607,302 | 3/1997 | Garrison et al. | 433/149 |
| 6,007,334 | * 12/1999 | Suhonen | 433/39 |

* cited by examiner

Primary Examiner—John J. Wilson
Assistant Examiner—Melba Bumgarner
(74) Attorney, Agent, or Firm—Young & Thompson

(57) ABSTRACT

The device for the retention and the adaptation of a matrix to the treated portion of a tooth includes a tightener clamp whose ends are each provided with an adaptation cushion having anchoring elements and adaptation elements, the cushion being destined to adapt to the contour of the border area of the cavity of the treated tooth portion in a formfitting manner. Such a device effectively prevents the formation of proximal excesses in composite fillings.

11 Claims, 6 Drawing Sheets

DEVICE FOR THE RETENTION AND ADAPTATION OF A MATRIX FOR DENTAL RESTORATIONS

BACKGROUND OF THE INVENTION

The present invention refers to a device for the retention and the adaptation of a matrix to the treated portion of a tooth, comprising a tightener clamp for the retention of a matrix, in particular of a proximal matrix system.

U.S. Pat. No. 5,607,302 describes a matrix retainer for dental restorations whose aim is to ensure an optimum contact with the adjacent tooth. This matrix tightener is mainly composed of a ring shaped tightener which operates with strong resilience. Its tips are spherical or cylindrical and correspond to a transversally extending ring, while the tips are anchored by engagement in undercuts of the tooth or by means of a frictional coating. This requires relatively high clamping forces, and the action of the tightener tips upon the matrix is only punctual, so that the resulting adaptation of the matrix to the tooth contour is insufficient. Also, similar products are available where the spherical tips of a tightener act upon a matrix.

SUMMARY OF THE INVENTION

On the background of this prior art, it is the object of the present invention to provide a device for the retention of a matrix for dental restorations which requires a lower contact pressure, on one hand, and on the other hand, which allows a tight lateral adaptation of the adjacent matrix portion, thus avoiding excess filling material mainly in the lateral and in the lateral cervical border area of the cavity.

This object is attained by a device wherein the ends of the tightener clamp are each provided with a wedge-shaped cushion whose point is destined to engage between the treated tooth and the adjacent tooth and which comprises an adaptation element or an adaptation side in order to press the matrix to the contour of the border area of the cavity of the treated tooth in a formfitting manner. Further advantages and embodiments are defined in the dependent claims.

BRIEF DESCRIPTION OF THE DRAWINGS

This invention will be explained in more detail hereinafter with reference to a drawing of an exemplary embodiment.

DETAILED DESCRIPTION OF THE INVENTION

Figure 1:
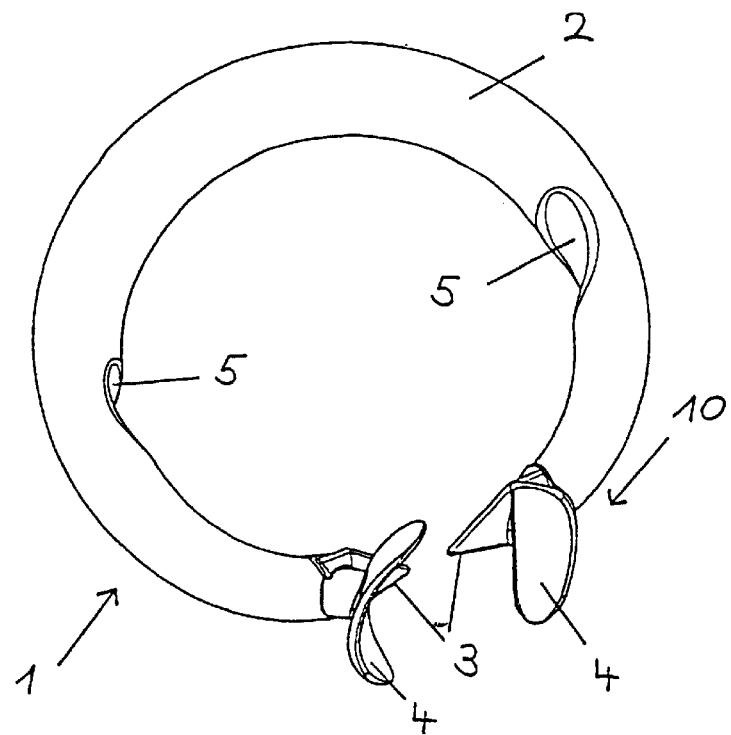
FIG. 1 shows a perspective view of a first embodiment of the device of the invention.

The device 1 for the retention and adaptation of a matrix according to FIG. 1 essentially consists of a tightener clamp 2, anchoring elements 3, and adaptation elements 4, the anchoring and adaptation elements jointly forming shaped cushions 10. Tightener clamp 2 is in the form of an open ring of plastic material or metal and is provided with two openings 5 for the insertion of a tensioning tool, which in the correct position of the tightener clamp extend at an angle α of 50° to 70° with respect to a plane through the center of the tightener clamp and perpendicularly to the occlusal surface, see FIG. 2. The tensioning tool may be commercially available rubber dam pliers or another spreading device in the form of tensioning pliers.

Such a tensioning tool could e.g. be similar to a clothespin. It serves the purpose of spreading apart the tightener clamp when it is being applied to the tooth and of releasing it when it is in the desired position, after which the tool is removed. It may be found to be useful if the adaptation elements are removably, resp. exchangeably attached to the tightener clamp.

Anchoring elements 3 serve to bring about a buccal resp. oral tensioning, i.e. a lateral wedging of the cushions, and at the same time to press the adaptation elements onto the tooth surface on both sides of the interdental border of the cavity. The thin plastic material or steel layer of matrix 16 is thereby individually adapted to the contour of the lateral border area of the cavity resp. in the area near the intact tooth substance, see FIG. 2 which illustrates the treated tooth 7, cavity 8, and the adjacent tooth 9.

In addition to the matrix adaptation, the matrix is pushed towards the proximal contact area without being pulled away. The area covered by the matrix is thereby molded in a convex shape. The principle of the matrix adaptation avoids to avoid the formation of proximal material excess and thus the application of injectable filling materials of medium viscosity. More particularly, the device provides a superficial adaptation of the matrix to convex tooth areas without gaps between tooth 7 and matrix 16.

Figure 2:
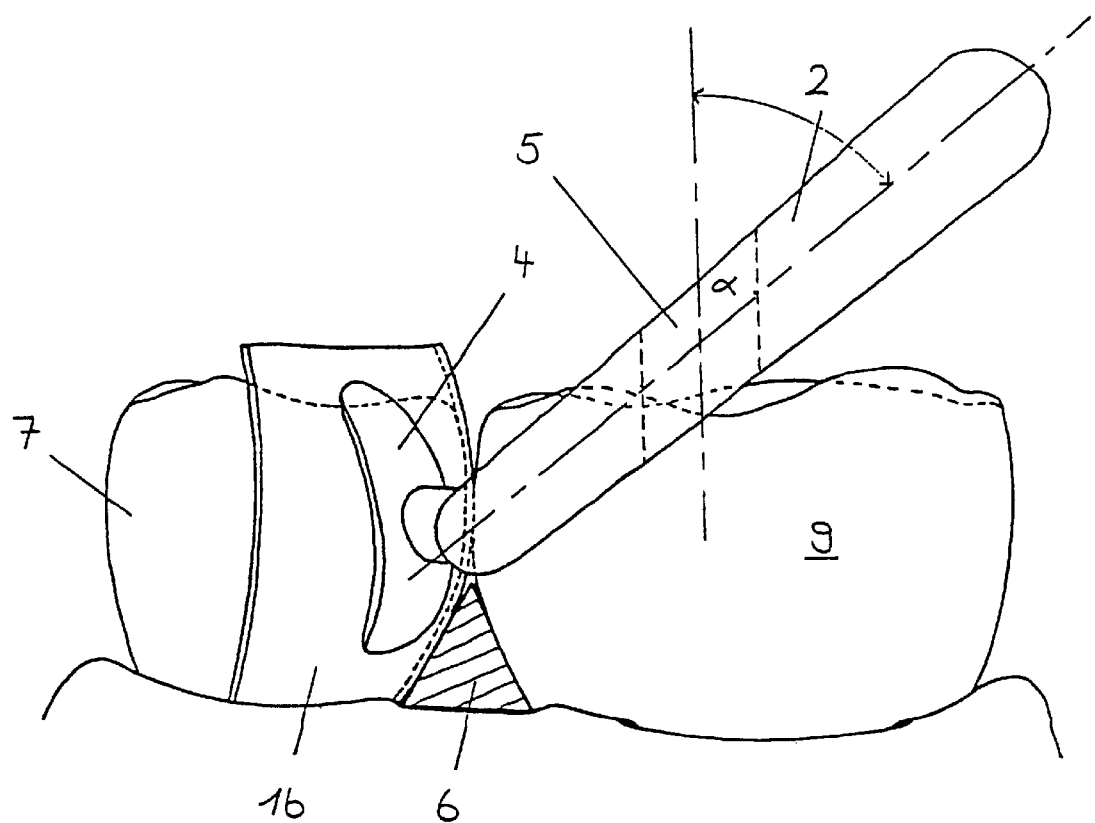
FIG. 2 shows the application of the device of FIG. 1 on two adjacent teeth in an occlusal view.
Figure 3:
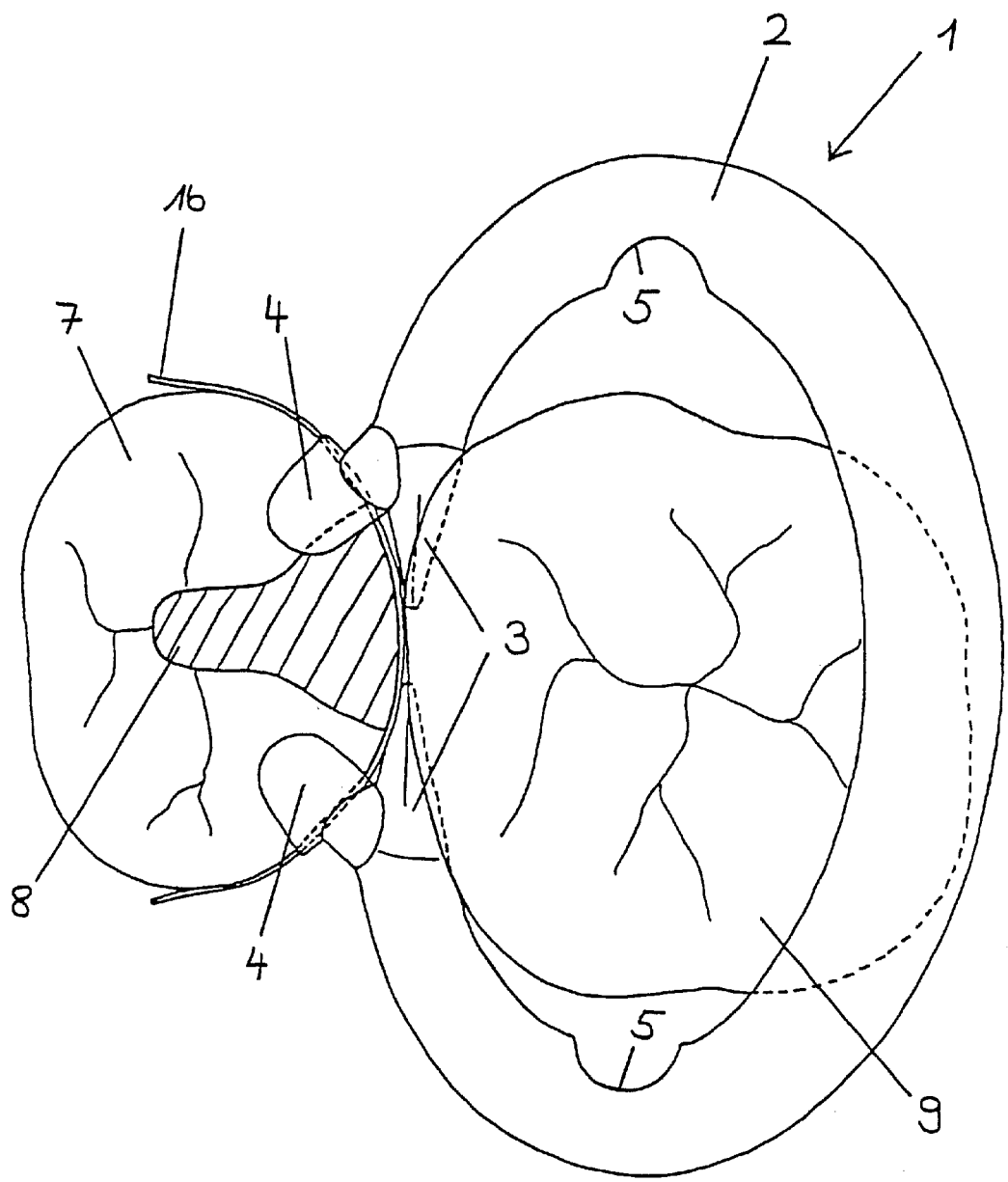
FIG. 3 shows the lateral view of FIG. 2.

The cervical adaptation of the matrix to the tooth and the separation of the proximal contact is obtained in a conventional manner by wooden or transparent plastic wedges 6, see FIG. 2.

Figure 4:
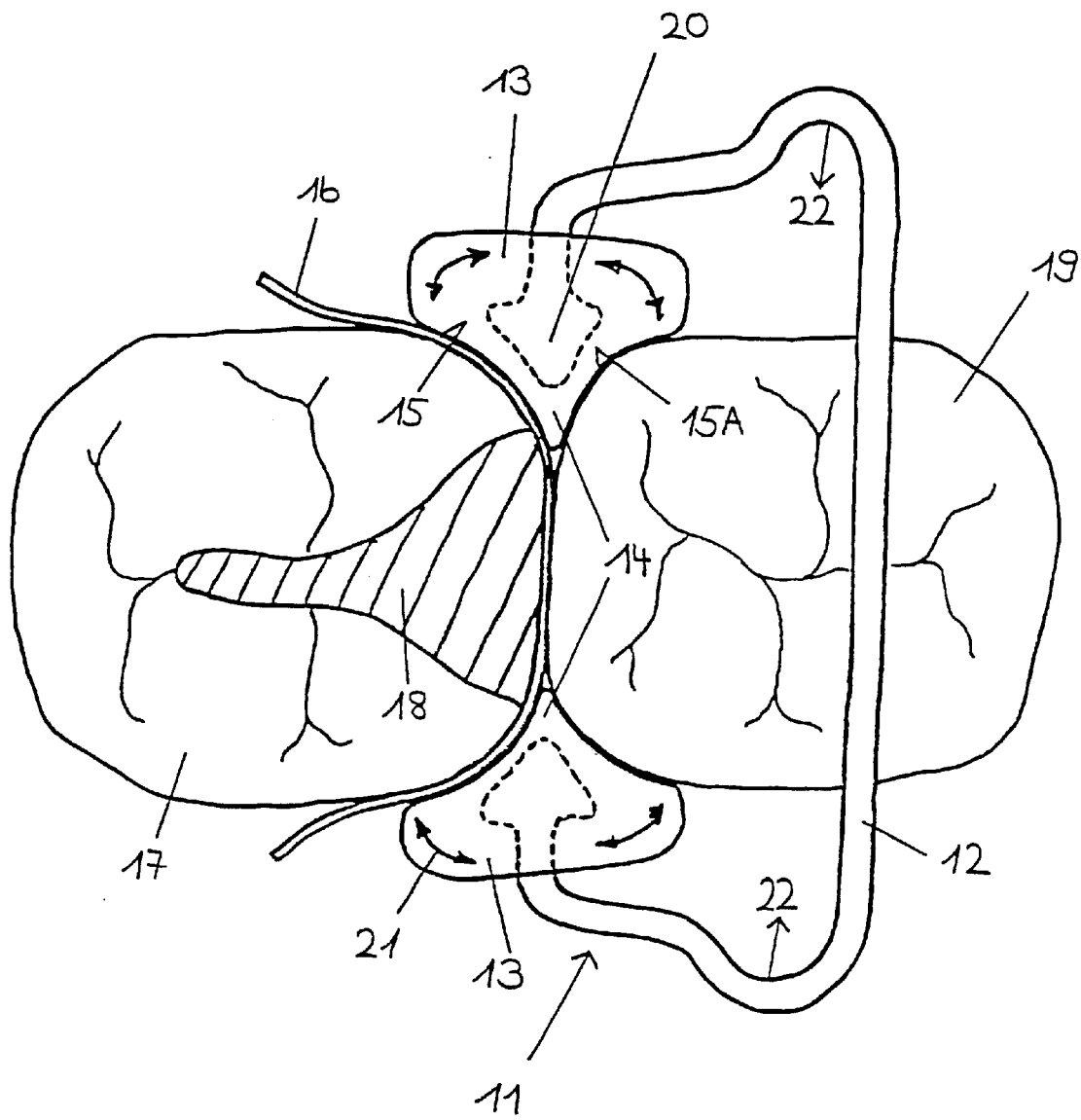
FIG. 4 shows an occlusal view of a second embodiment.

In the embodiment of FIG. 4, a tightening device 11 is shown whose tightener clamp 12 is provided with two attachable and exchangeable silicon cushions 13. As shown in FIG. 4, cushions 13 have an approximately wedge-shaped ground plan, point 14 of the wedge being positioned between two teeth, and the formfitting adaptation side 15 of the wedge maintaining matrix band 16 on its entire surface while the other shank 15A rests on the adjacent tooth 19.

In FIG. 4, which is an occlusal view, the treated tooth 17 with cavity 18, which is to be filled with a composite filling, is shown on the left. In this example, the adjacent tooth 19 on the right does not require a treatment. If cushion 13 is articulated on holder 20 of the tightener clamp, a self-adjusting capability of the cushion results, as symbolized by double arrows 21. Arrows 22 represent the contact points of the tensioning pliers. Instead of silicon cushions, cushions of another resilient material may be used, while it should be noted that the cushions must be transparent if the tightening device is intended for composite materials.

Figure 5:
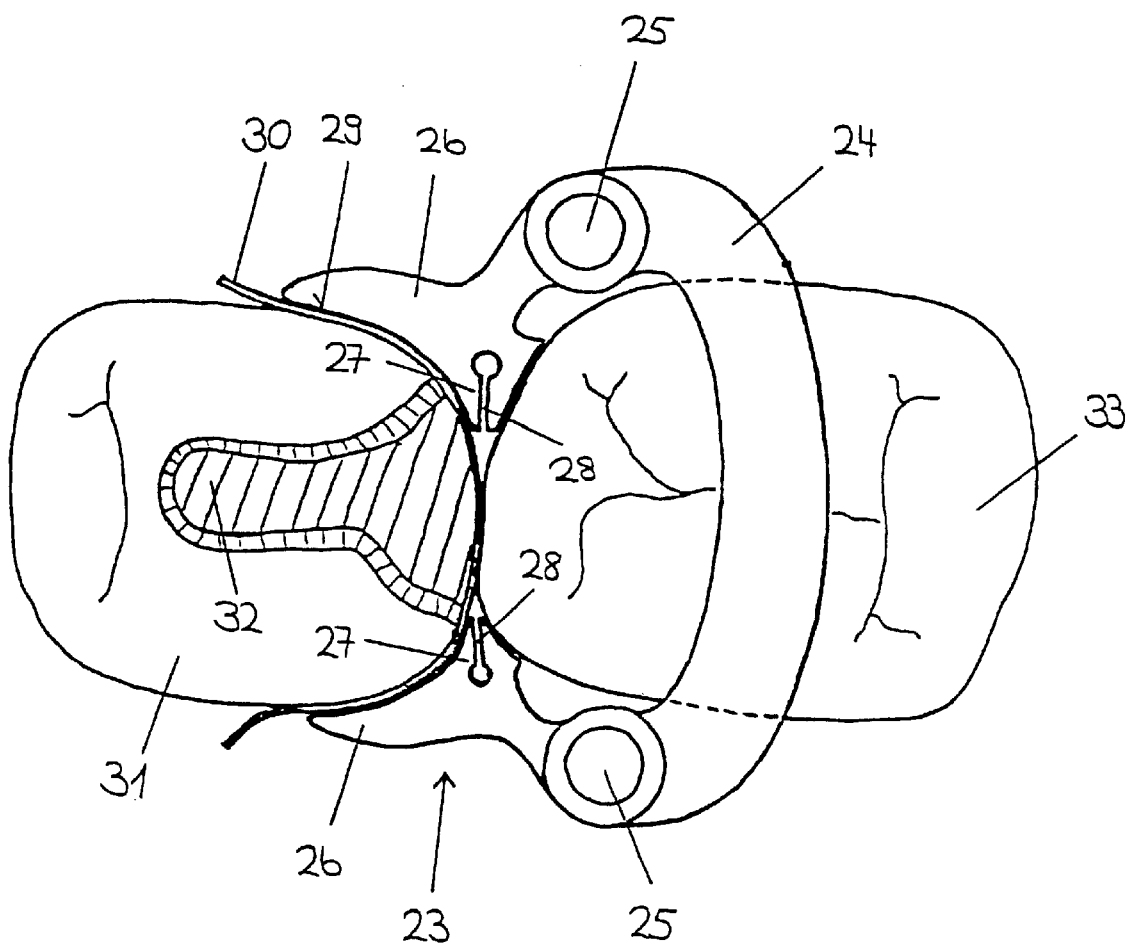
FIG. 5 shows an occlusal view of another embodiment.

Tightening device 23 according to FIG. 5 comprises a tightener clamp 24 provided with openings 25 for the insertion of tensioning pliers whose inclination a with respect to the ring plane is the same as in the first embodiment, each end comprising a shaped cushion 26. The shaped cushions 26 are articulated and removably attached to tightener clamp 24, as the case may be, and they comprise a wedge-shaped portion having a slot 28 in order to provide a better adaptation to different tooth shapes. The cushions are preferably made of a silicon material or of a material having similar elastic and, of course, dental hygienic properties. The wedge-shaped portion is followed by an adaptation portion 29 in order to press the entire surface of matrix 30 against tooth 31 with cavity 32 in a formfitting manner. On the other side, the cushion rests on the adjacent tooth 33 in a formfitting manner.

The matrix bands resp. matrix foils for the generally light-hardening filling materials must be transparent ones. Partial interdental matrixes, so-called partial matrixes, are suitable for individual interdental treatments. For a better adaptation to the tooth shape, different curvatures e.g. for molars, premolars, or for the anterior teeth may be useful. Short strip-shaped metal portions of the matrix may serve for its interdental insertion, the metal portion being torn off at the connecting point when it is in position. Also, for multiple surface cavities, open matrixes may be used, e.g. with metallic inserting aids. Furthermore, adhesive, light-hardenable plastic materials whose consistence allows spraying may be used for individual sealing and adapting operations.

The tightening cushions need not necessarily be made of a plastic material or of silicon, but they can also consist of a correspondingly shaped metal wire having an adhesive coating, the cushion forming a wedge- or a V-shaped form together with the tightener clamp ends to which the cushions are attached. The contact points of the cushions are generally in undercuts below the tooth equator in order to keep them from slipping off in the occlusal direction. The cushions are so designed that they anchor themselves when they are pressed into undercut buccal, lingual, or interdental-cervical areas.

Figure 6:
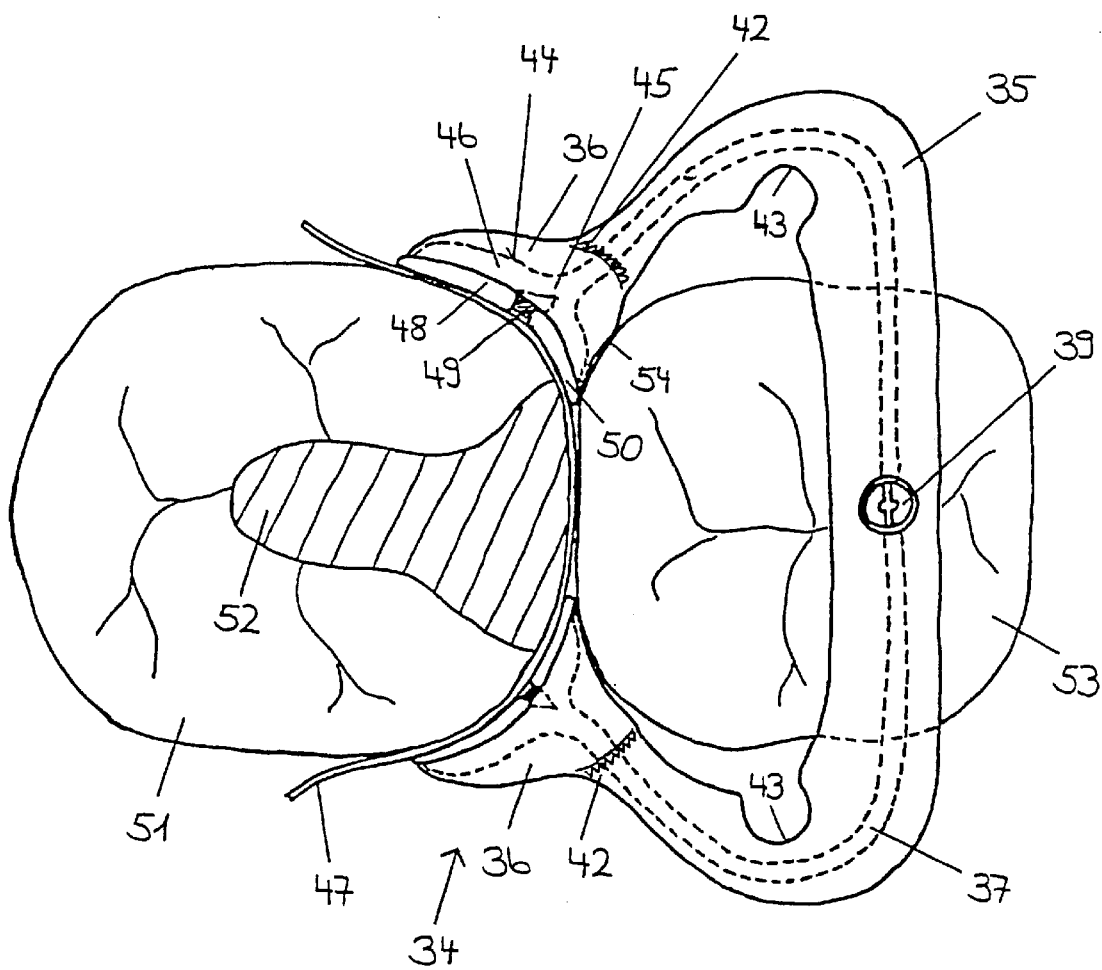
FIG. 6 shows an occlusal view of a embodiment actuated by pneumatic means.
Figure 7:
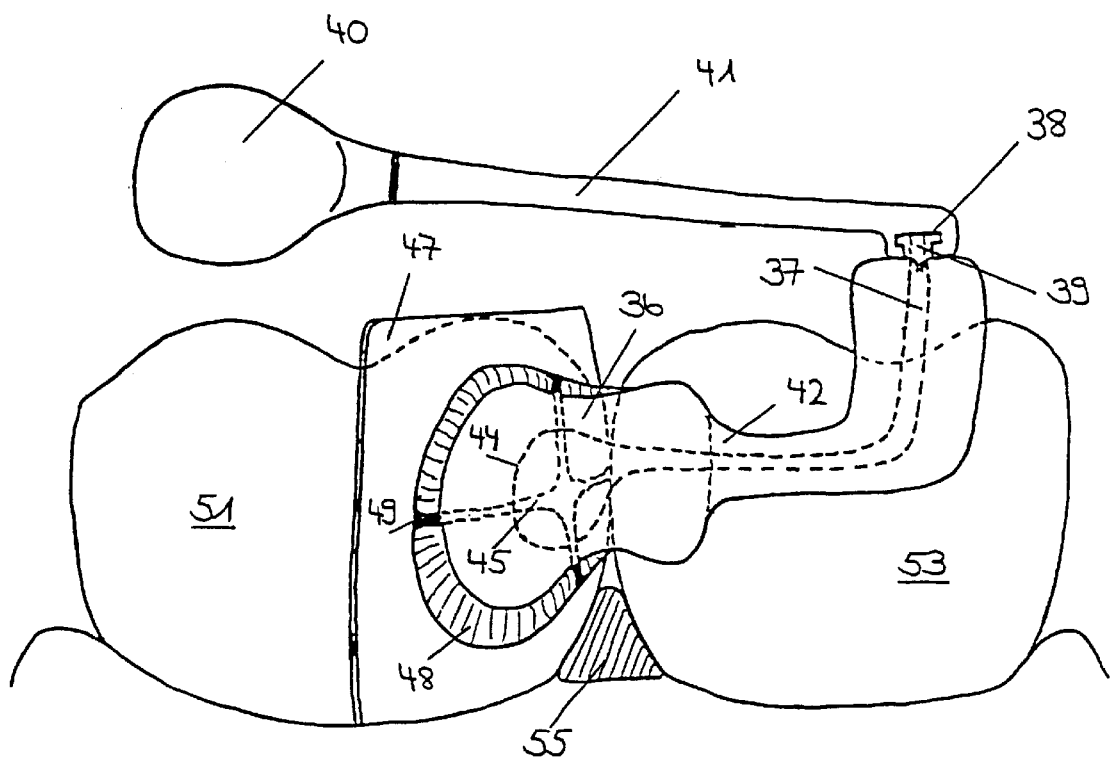
FIG. 7 shows the device of FIG. 6 in a lateral view.

FIGS. 6 and 7 show a device for the retention and adaptation of a matrix where the matrix can be better adapted and fitted by means of a pneumatically produced pressure. Like the preceding devices, device 34 comprises a tightener clamp 35 whose ends are provided with shaped cushions 36. Tightener clamp 35 is hollow and comprises an air channel 37 having an inlet 38 and a check valve 39, and a bellows 40 having a feed pipe 41 which is capable of being connected to inlet 38. The tightener clamp is preferably manufactured from a transparent plastic material and comprises a softer portion 42 at the transition to the cushion which serves as an articulation.

The tightener clamp further comprises two contact points 43 for the attachment of the tensioning pliers. Shaped cushion 36 essentially consists of a transparent, relatively rigid plastic cap 44 which is fastened to the softer portion and provided with an air passage 45 ending in an air cushion 46. Air cushion 46 may have a rubber-like surface which acts upon matrix 47 directly, or the air cushion may be followed by rubber segments 48 which are connected to each other by a respective joint 49 and act upon matrix 47. According to the occlusal view of FIG. 6, the cushion comprises a wedge-shaped portion 50 which engages between the tooth 51 with cavity 52 requiring restoration and the adjacent tooth 53, the wedge providing a formfitting pressure upon the matrix by the adaptation side with rubber segments 48 and by an abutment 54 which rests on the intact tooth 53. By inflating the air cushion, it is possible to increase the clamping force of the tightener clamp and to provide an even better adaptation of the cushion resp. of the rubber segments to the shape of the tooth in order to tightly and formfittingly adapt the thin matrix foil to the tooth.

FIG. 7 also schematically shows a conventional wedge 55 in cross-section. It may be a transparent, light-guiding wedge, possibly with wooden or plastic parts, which can be applied together with the lateral adaptation system without interfering therewith. For such purposes, it may be necessary to modify conventional wedges, i.e. mainly to reduce their cervical-occlusal thickness, whereby the modified wedges become trapezoidal in cross-section.

What is claimed is:

1. Device for the retention and the adaptation of a matrix to the treated portion of a tooth, comprising a tightener clamp for the retention of a matrix, wherein the ends of said tightener clamp are each provided with a cushion whose point is destined to engage between the treated tooth and the adjacent tooth and which comprises an adaptation element or an adaptation side in order to press said matrix to the contour of the border area of the cavity of the treated tooth in a formfitting manner and an anchoring element located adjacent said adaptation element for pressing said adaptation element onto a tooth surface.

2. The device of claim 1, wherein said cushions are made of a transparent plastic material.

3. The device of claim 1, wherein said cushions are attached to the ends of said tightener clamp in a removable and/or articulated manner.

4. The device of claim 1, wherein said tightener clamp is provided with two inserting openings or two contact areas for the purpose of spreading it apart by means of tensioning pliers, the inserting openings having two parallel edges which are inclined at an angle (a) of 50° to 70° with respect to a plane through the center of the tightener clamp.

5. The device of claim 1, wherein said tightener clamp is made of metal or of a plastic material.

6. The device of claim 1, wherein the cushions are made of silicon.

7. Device for the retention and the adaptation of a matrix to the treated portion of a tooth, comprising a tightener clamp for the retention of a matrix, wherein the ends of said tightener clamp are each provided with a cushion whose point is destined to engage between the treated tooth and the adjacent tooth and which comprises an adaptation element or an adaptation side in order to press said matrix to the contour of the border area of the cavity of the treated tooth in a formfitting manner, wherein said cushions comprise a slot in order to provide a better adaptation.

8. Device for the retention and the adaptation of a matrix to the treated portion of a tooth, comprising a tightener clamp for the retention of a matrix, wherein the ends of said tightener clamp are each provided with a cushion whose point is destined to engage between the treated tooth and the adjacent tooth and which comprises an adaptation element or an adaptation side in order to press said matrix to the contour of the border area of the cavity of the treated tooth in a formfitting manner, wherein said cushions each comprise an inflatable air cushion.

9. The device of claim 8, wherein an inflating device comprising a bellows is connected to said air cushions by a pipe to an inlet of the tightener clamp which is provided with a check valve.

10. The device of claim 8, wherein the transition between the tightener clamp and the cushion comprises a softer portion which serves as an articulation.

11. A device for retention and adaptation of a matrix to a treated portion of a tooth, comprising:

a tightener clamp for retention of a matrix;

two resilient and conformal cushions, one of said two cushions attached on each of two ends of said clamp, said two cushions being adapted to engage between the treated tooth and an adjacent tooth and to conform the matrix to a contour of a border area of a cavity of the treated tooth; and an anchoring element located adjacent each of said two cushions for pressing the associated one of the two cushions onto a tooth surface.

* * * * *